United States Patent [19]

Burghart et al.

[11] Patent Number: 4,863,720
[45] Date of Patent: Sep. 5, 1989

[54] PHARMACEUTICAL PREPARATION AND METHODS FOR ITS PRODUCTION

[76] Inventors: Walter Burghart, A-1030 Vienna, Salmgasse 4, Vienna, Austria; Kurt Burghart, D-2217 Rosdorf, Saegeberg 8, Rosdorf, Fed. Rep. of Germany

[21] Appl. No.: 127,292

[22] PCT Filed: Mar. 10, 1987

[86] PCT No.: PCT/AT87/00015
§ 371 Date: Nov. 10, 1987
§ 102(e) Date: Nov. 10, 1987

[87] PCT Pub. No.: WO87/05210
PCT Pub. Date: Sep. 11, 1987

[30] Foreign Application Priority Data

Mar. 10, 1986 [AT] Austria .................................. A621/86

[51] Int. Cl.⁴ .............................................. A61L 9/04
[52] U.S. Cl. ........................................ 424/45; 424/78; 424/81; 424/923
[58] Field of Search ..................... 424/45, 78, 81, 923

[56] References Cited

FOREIGN PATENT DOCUMENTS 856652 4/1977 Belgium .
0856652 10/1977 Belgium .
2830044 1/1979 Fed. Rep. of Germany .
2396547 3/1979 France .
81/03421 5/1981 PCT Int'l Appl. .

Primary Examiner—Thurman K. Page
Assistant Examiner—P. L. Prater
Attorney, Agent, or Firm—Nixon & Vanderhye

[57] ABSTRACT

A sprayable pharmaceutical preparation available in doses in aerosol containers comprises an active ingredient dissolved in polyalkylene glycol, and/or polyethylene glycol, and/or fatty glycolic acid ester of glycerine-polyethylene such as glycerine-polyethyleneglycol oxyoleate and/or glycerine-polyethyleneglycol oxystearate, and/or partial fatty acid esters of sorbitol or polyhydroxyethylene sorbitol, and/or polyvinylpyrrolidones, and/or polyvinyl alcohols, and/or fatty alcohol ethers of polyhydroxyethylene or fatty acid esters of polyhydroxyethylene and/or condensates of polyhydroxyethylen-polyhydroxypropylene and/or propylene carbonate, mixed with ethanol, substituted if necessary at least partially with middle chain diglyceride and/or triglyceride of fatty acids, and with a pharmacologically acceptable propellant, in particular halogenated hydrocarbons.

16 Claims, 1 Drawing Sheet

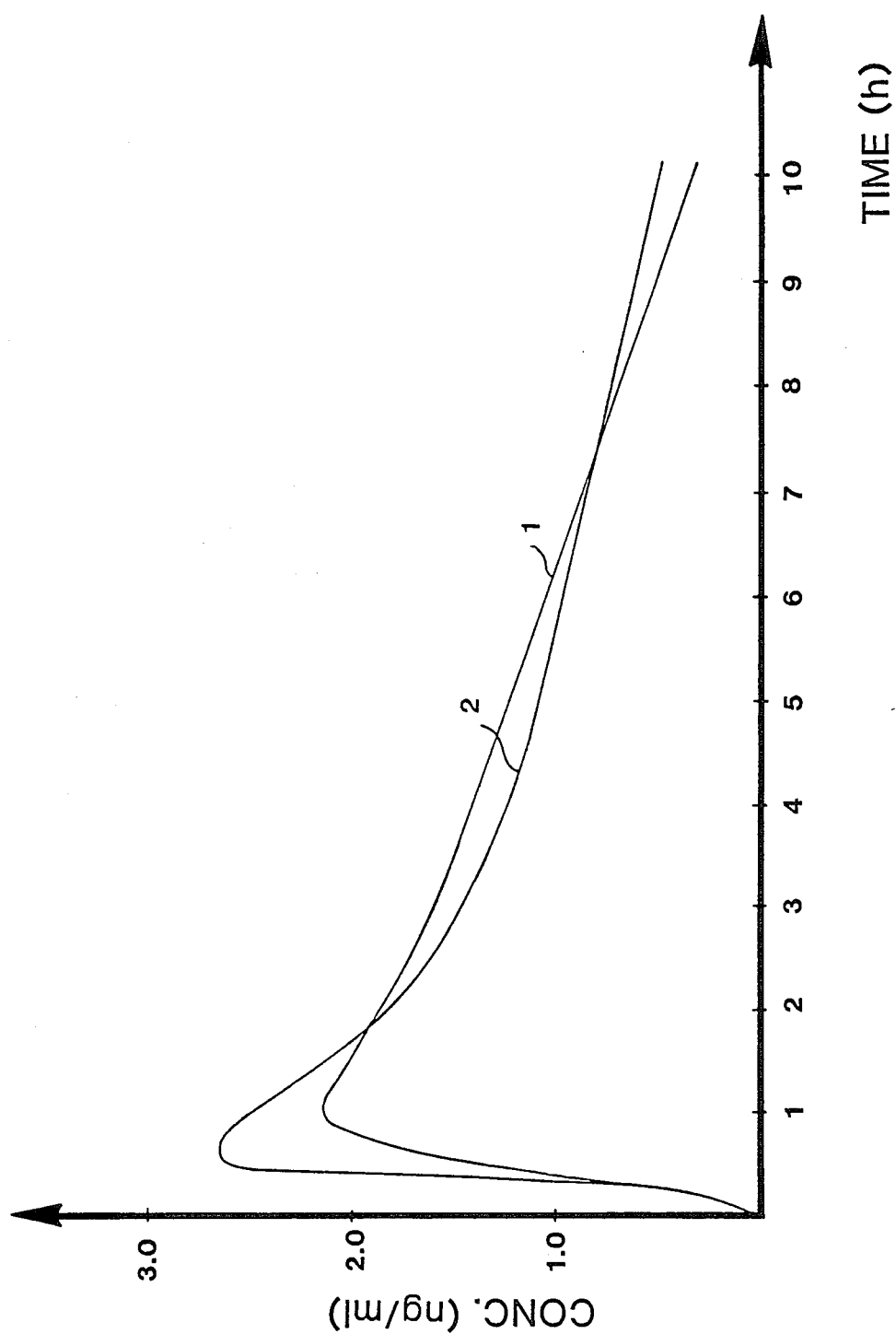

PHARMACEUTICAL PREPARATION AND METHODS FOR ITS PRODUCTION

The invention relates to a pharmaceutical preparation with benzodiazepines as active ingredients and to methods for its production.

Benzodiazepines, in particular the 1,3-Dihydro-7-nitro-5-phenyl-2H-1,4-benzodiazepine-2-one or Diazepam (7-Chloro-1,3-dihydro-1-methyl-5-phenyl-2H-1,4-benzodiazepine-2-one) or Flurazepam 7-Chloro-1-2-(diethylamino)ethyl-5-(2-fluoro-phenyl)-1H-1,4-benzodiazepine-2(3H)-one or Triazolam, 8-Chloro-6-(o-chlorophenyl)-1-methyl-4H-s-triazolo-[4,3-a]-[1,4]benzodiazepine or Alprazolam (8-chloro-1-methyl-6-phenyl-4H-1,2,4-triazolo[4,3-a][1,4]-benzodiazepine) or Midazolam (8-chloro-6-(2-fluoro-phenyl)-1-methyl-4 H-imidazolo[1,5]-[1,4]-benzodiazepine) are widely distributed as sedatives and are used especially in the case of disturbed sleep, anxiety states in a status epilepticus, spasms of central nervous origin etc. Benzodiazepines are generally used in form of tablets, whereby the onset of activity usually occur with a delay. Especially the previous ingestion of food may lead to a significant retardation of the therapeutic effect. A formulation with a more rapid absorption and thus a more rapid onset of activity was proposed in form of drops. Such drops require a not trembling hand for dosage and are therefore not intended for many patients especially by using it in connection with status epilepticus or spasms of central nervous origin. Pharmaceutical preparations containing benzodiazepines which are applied in form of drops or soft gelatine capsules have already been described in the DE-OS No. 28 30 044.

The aim of the present invention is to prepare a form of administration of these well known drugs which guarantees a higher precision of the dosage, a more rapid bioavailability and especially an independence of the absorption from the previous intake of food. Moreover the preparation should be largely protected against manipulation. Because of the wide-spreading use of these drugs attempts of adding toxic substances to presentations like tablets or drops are possible. Moreover a relative slow onset of activity as in the case of a tablet formulation may cause an unnecessary high drug level in the patient, which can be prevented by an acceleration of the onset of effect. Especially patients suffering from insomnia and anxiety states tend to increase the dose in the case of an insufficient onset of activity. Similarly an inaccurate counting by administering the drug in form of drops may cause an overdosage.

Thus the present invention aims at avoiding the above mentioned disadvantages and in particular preparing a formulation with a very rapid onset of activity, a minimum risk of manipulation, an improvement of the precision of the dosage and altogether a reduction of the patient strain caused by an unnecessary high dosage.

To fulfil these demands the preparation of the present invention with benzodiazepines as active ingredients consists essentially of a solution of the active ingredient in polyalkylene glycol, and/or polyethylene glycol, and/or glycerine-polyethylene glycol oxy fatty acid esters such as glycerine-polyethyleneglycol oxyoleate and/or glycerine-polyethylene glycol oxystearate, and-/or partial fatty acid esters of sorbitol and polyhydroxyethylene-sorbitol respectively, and/or polyvinylpyrrolindones, and/or polyvinyl alcohols, and/or polyhydroxyethylene fatty alcohol ethers and polyhydroxyethylene fatty acid esters respectively and/or polyhydroxyethylene-polyhydroxypropylene condensates and/or propylene carbonate which is filled in aerosol containers in combination with ethanol, which can be replaced at least in part by medium-chain fatty acid di-and/or -triglycerides and a pharmacologically inert propellant, in particular halogenated hydrocarbons and can be sprayed as a metered dose aerosol.

Due to the selection of the solvent proposed in the present invention such an aerosol surprisingly has shown an extremely rapid absorption, a much more rapid onset of activity and a more uniform action than other forms of administration. Due to the more rapid onset of activity the risk of an arbitrary dose build up by the patient is diminished and the load caused by an unnecessary high dosage is considerably reduced. By means of a metered valve the precise dosage of the spray jets is possible. Thus the precision of the dosage of such an aerosol is much superior or that accomplished by the counting of drops. The benzodiazepines used as active ingredients usually demand a protection from light which will automatically by guaranteed by measures of filing the active ingredient together with the above mentioned solvents, ethanol and propellant in light-tight containers. Due to the sublingual administration also the risk of a drug abuse is considerably reduced because after application of a great number of spray jets only an oral absorption is possible, thus a considerable lower plasma level and therapeutic effect can be expected. The possibility to administer lower doses, which cause reduced load of the liver is a further advantage of the sublingual application, especially in patients with an impaired liver function.

Especially preferred in the field of the present invention is a pharmaceutical preparation characterized through the fact, that related to a volume of 100 $\mu$l each spray jet contains 0,1–5 mg active ingredient, 3–50 mg, especially 5–25 mg polyethylene glycol, and/or glycerine-polyethyleneglycoloxystearate, and/or partial fatty acid esters of sorbitol and polyhydroxyethylene sorbitol respectively, and/or polyvinylpyrrolidone, and/or polyvinyl alcohols, and/or polyhydroxyethylene fatty alcohol ethers and polyhydroxyethylene fatty acid esters respectively and/or polyhydroxyethylene-polyhydroxypropylene condensates, 10–40 mg, especially 15–30 mg ethanol, remaining part propellant and optionally pharmaceutical acceptable adjuvants and/or flavours.

In the case of spray jets with a volume considerably exceeds 100 $\mu$l, the dosage of the active ingredients per 100 $\mu$l can be chosen close to the lower limit mentioned above.

Especially preferred in the field of the present invention is a pharmaceutical preparation, which can be characterized by use of pharmacologically potent benzodiazepines, in particular Triazolam as active ingredient, whereby each 100 mg solution or each spray jet contains 0,05–0,3 mg Triazolam. Due to the use of pharmacologically potent benzodiazepines, in particular Triazolam as active ingredient a reduction of the quantity of the employed active substance by a factor of about two in comparison with other known dosages of the same active substance in form of a capsule or a tablet or with other diazepines used a active components can be achieved.

Preferably used in a pharmaceutical preparation are benzodiazepines, in particular Triazolam and polyethylene glycol as solubilising agent in a ratio between 1:20 and 1:60, preferably 1:25 and 1:35.

Preferably used in a pharmaceutical preparation are benzodiazepines, in particular Diazepam and propylene carbonate and/or glycerin-polyethylene glycol oxystearate and/or medium-chain fatty acid diglycerides and-/or triglycerides as solubilising agent in a ratio between 1:10 and 1:20.

The process for preparing of such a preparation with benzodiazepines as active ingredient according to the present invention is mainly characterized through the fact, that 0,1–5 parts by weight diazepines are dissoluted in 3–50 parts by weight of a solvent selected from the group polyalkylene glycol, polyethylene glycol and/or glycerine-polyethylene glycol oxy fatty acid esters such as glycerine-polyethyleneglycol oxyoleate and/or glycerine-polyethyleneglycol oxystearate and/or partial fatty acid esters of sorbitol and polyhydroxyethylene sorbitol respectively and/or polyvinylpyrrolidones, and/or polyvinyl alcohols, and/or polyhydroxyethylene fatty alcohol ethers and polyhydroxyethylene fatty acid esters respectively and/or polyhydroxyethylene-polyhydroxypropylene condensates and/or propylene carbonate and with 10–40 parts by weight of ethanol which is optionally at least partly replaced by medium-chain fatty acid di- and/or -triglycerides and 20–70 parts by weight of a propellant, on the basis of halogenated hydrocarbons is filled in containers for the administration as aerosol with spray jets between 35 and 500 µl The aerosol according to this invention is preferably administered sublingually, whereby the extremely rapid onset of activity is guaranteed in this way.

Subsequently the invention is characterized more detailed on the basis of performed examples, whereby the benzodiazepines 8-Chloro-5-(o-chlorophenyl)-1-methyl-4H-s-triazolo-[4,3-a]-[1,4]benzodiazepine (Triazolam) and 7-Chloro-1,3-dihydro-1-methyl-5-phenyl-2H-1,4-benzodiazepine-2-one (Diazepam) were employed as active ingredients.

EXAMPLE 1

A solution was prepared containing specified quantities of the following components per 150 mg aerosol:

| Diazepam | 2 mg |
|---|---|
| Polyethylene glycol 600 | 28 mg |
| Glycerine-polyethylene-glycoloxystearate | 28 mg |
| Ethanol | 30 mg |
| Propellant | 90 mg |
| | 150 mg |

Dichlorodifluoromethane optionally mixed with Trichloromonofluoromethane was used as the propellant in all examples.

The mixture resulted in a complete, stable solution which could be sprayed in accurate doses without problems. Spray jets of each 150 mg aerosol proved to be particularly effective. The dosage weight of 150 mg could be reproduced at any time by means of the employed spraying device, a brown coloured glass bottle or an aluminium can, both equipped with a 150 mg dosage valve.

EXAMPLE 2

A solution was prepared containing specified quantities of the following components per 150 mg aerosol:

| Diazepam | 5 mg |
|---|---|
| Propylene carbonate | 40 mg |
| Medium-chain triglycerides of fatty acids | 20 mg |
| Glycerine-polyethylene-glycoloxystearate | 10 mg |
| Ethanol | 20 mg |
| Propellant | 55 mg |
| | 150 mg |

The mixture resulted in a complete, stable solution which could be sprayed in accurate doses without problems. Spray jets of each 150 mg aerosol proved to be particularly effective.

The dosage weight of 150 mg could be reproduced at any time using the spraying device mentioned in Example 1.

EXAMPLE 3

A solution was prepared containing specified quantities of the following components per 100 mg aerosol:

| Triazolam | 0,25 mg |
|---|---|
| Polyethylene glycol 400 | 7,00 mg |
| Ethanol | 32,00 mg |
| Ethyl vanillin | 0,20 mg |
| Glycerine | 0,40 mg |
| Sodium saccharinate | 0,15 mg |
| Propellant | 60,00 mg |
| | 100,00 mg |

The mixture resulted in a complete, stable solution which could be sprayed in accurate doses without problems. Spray jets of each 90 mg aerosol proved to be particularly effective.

The dosage weight of 90 mg could be reproduced at any time by means of the spraying device mentioned in Eexample 1 using a dosage valve with a volume of 100 µl.

EXAMPLE 4

A solution was prepared containing specified quantities of the following components per 100 mg aerosol:

| Triazolam | 0,125 mg |
|---|---|
| Polyethylene glycol 400 | 4,000 mg |
| Ethanol | 20,000 mg |
| Ethyl vanillin | 0,150 mg |
| Glycerine | 0,300 mg |
| Sodium saccharinate | 0,125 mg |
| Propellant | 75,300 mg |
| | 100,000 mg |

The mixture resulted in a complete, stable solution which could be sprayed very well. Spray jets of each 120 mg aerosol proved to possess a particularly rapid onset of activity.

The dosage weight of 120 mg could be reproduced at any time using the spraying device mentioned in Example 3.

EXAMPLE 5

A solution was prepared containing specified quantities of the following components per 100 mg aerosol:

| Triazolam | 0,125 mg |
|---|---|
| Polyethylene glycol 400 | 6,000 mg |
| Ethanol | 23,000 mg |
| Ethyl vanillin | 0,150 mg |

| -continued | |
|---|---|
| Glycerine | 0,300 mg |
| Sodium saccharinate | 0,125 mg |
| Propellant | 70,300 mg |
| | 100,000 mg |

The mixture resulted in a complete, stable solution which could be sprayed in accurate doses without problems Spray jets of each 110 mg aerosol proved to be particularly effective.

The dosage weight of 110 mg could be reproduced at any time using the spraying device mentioned in Example 3.

EXAMPLE 6

A solution was prepared containing specified quantities of the following components per 100 mg aerosol:

| Triazolam | 0,125 mg |
|---|---|
| Polyethylene glycol 400 | 7,000 mg |
| Ethanol | 25,000 mg |
| Ethyl vanillin | 0,150 mg |
| Glycerine | 0,300 mg |
| Sodium saccharinate | 0,125 mg |
| Propellant | 67,300 mg |
| | 100,000 mg |

The mixture resulted in a complete, stable solution which could be sprayed in accurate doses without problems Spray jets of each 100 mg aerosol proved to be particularly effective.

The dosage weight of 100 mg could be reproduced at any time.

BRIEF DESCRIPTION OF THE DRAWING

The relative bioavailability of the formulation stated in the example was examined and is shown in the figure. Each curve represents the evaluated mean value.

The measured values (ng/ml) are indicated on the ordinate versus the time (h) on the abscissa It is evident from the figure, that the bioavailability after administration of two spray jets (curve 1) is somewhat lower than that obtained after administration of a tablet with 0,5 mg Triazolam (curve 2). However, the two spray jets contained a dose of only 0,25 mg Triazolam.

7 hours after administration the areas under both curves are approximately identical, although the dosage after administration of two spray jets was only half of that after administration of the tablet.g,16

EXAMPLE 7

In order to evaluate how much the content of the solubilising agent Polyethylene glycol 400 may be reduced to gain still a complete solution of Triazolam, an aerosol was prepared containing specified quantities of the following components:

| Triazolam | 0,50 mg |
|---|---|
| Polyethylene glycol 400 | 6,00 mg |
| Ethanol | 32,00 mg |
| Ethyl vanillin | 0,30 mg |
| Glycerine | 1,00 mg |
| Sodium saccharinate | 0,20 mg |
| Propellant | 60,00 mg |
| | 100,00 mg |

It was not possible to dissolve the specified quantity of Triazolam in this formulation.

We claim:

1. A pharmaceutical preparation with benzodiazepines as active ingredients, said preparation comprising a solution of the active ingredient in a first solvent selected from the group consisting of a polyalklene glycol, glycerine-polyethylene glycol oxy fatty acid esters, partial fatty acid esters of sorbitol, partial fatty acid esters of polyhydroxyethylene-sorbitol, polyvinyl pyrrolidones, polyvinyl alcohols, polyhydroxyethylene fatty alcohol ethers, polyhydroxyethlene fatty acid esters, polyhydroxyethylenepolyhydroxyproplene condensates and propylene carbonate, and a second solvent which is ethanol which may be at least partly replaced by a compound selected from the group consisting of a medium-chain fatty acid diglyceride and a medium-chain fatty acid triglyceride, and a pharmacologically inert propellant, said preparation being filled in an aerosol container and being sprayable as a metered dose aerosol.

2. A pharmaceutical preparation according to claim 1, wherein said first solvent is polyethylene glycol.

3. A pharmaceutical preparation according to claim 1, wherein said glycerine-polyethylene glycol oxy fatty acid esters are selected from the group consisting of glycerinepolyethylene-glycol oxy oxyoleate and glycerine-polyethylene glycol oxy stearate.

4. A pharmaceutical preparation according to claim 1, wherein said pharmacologically inert propellant is a halogenated hydrocarbon.

5. A pharmaceutical preparation according to claim 1, wherein relative to a volume of 100 $\mu$l a spray jet contains 0.1–5 mg of active ingredient 3–50 mg of said first solvent selected from the group consisting of polyethylene glycol, glycerine-polyethyleneglycoloxystearate, partial fatty acid esters of sorbitol, partial fatty acid esters of polyhydroxyethlene-sorbitol, polyvinylpyrrolidone, polyvinyl alcohols, polyhydroxyethylene fatty alcohol ethers and polyhydroxyethylene fatty alcohol esters respectively and polyhydroxyethylene-polyhydroxypropylene condensates, 10–40 mg of ethanol, and the remaining part propellant and a pharmaceutically acceptable adjuvant or flavor.

6. A pharmaceutical preparation according to claim 5, wherein said first solvent is present in an amount of 5–25 mg.

7. A pharmaceutical preparation according to claim 5, wherein said ethanol is present in an amount of 15–30 mg.

8. A pharmaceutical preparation according to claim 1, wherein when said active ingredient is 8-chloro-6-(o-chlorophenyl)-1-methyl-4H-s-triazolo-[4,3-a]-[1,4] benzodiazepine, each 100 mg solution or each spray jet contains 0.05–0.3 mg of that active ingredient.

9. A pharmaceutical preparation according to claim 1, wherein benzodiazepines and polyethylene glycol are present in a weight ratio between 120 and 1:60.

10. A pharmaceutical preparation according to claim 9, wherein said benzodiazepine is 8-chloro-6-(o-chlorophenyl)-1-methyl-4H-s-triazolo-[4,3-a]-[1,4] benzodiazepine.

11. A pharmaceutical preparation according to claim 9, wherein said benzodiazepine and acid polyethlene glycol are present in a weight ratio between 1:25 and 1:35.

12. A pharmaceutical preparation according to claim 1, wherein benzodiapine and a first solvent selected from the group consisting of propylene carbonate, glycerine-poly-ethyleneglycol oxystearate and medium-chain fatty di- and - triglycerides are present in a weight ratio between 1:10 and 1:20.

13. A pharmaceutical preparation according to claim 12, wherein said denzodiazepine is 7-chloro-1,3-dihydro-1-methyl-5-phenyl-2H-1,4-benzodiazepine-2-one.

14. A process for preparing a pharmaceutical preparation with benzodiapines as the active ingredients, and process comprising the steps of:

dissolving 0.1 to 5 parts by weight of a benzodiazepine in 3 to 50 parts by weight of a first solvent selected from the group consisting of a polyalklene glycol, glycerine-polyethylene glycol oxy fatty acid esters, partial fatty acid esters of sorbitol, partial fatty acid esthers of polyhydroxyethylene-sorbitol, polyvinyl pyrrolidones, polyvinyl alcohols, polyhydroxyethylene fatty alcohol ethers, polyhydroxyethylene fatty acid esthers polyhydroxyethylenepolyhydroxyethylene condensates and propylene carbonate, and a second solvent which is ethanol which may be at least partly replaced by a compound selected from the group consisting of a dedium-chain fatty acid diglyceride and a medium-chain fatty acid triglyceride, and 20–70 parts by weight of propellant, on the basis of halogenated hydrocarbon; and filling the resulting solution in containers for administration as an aerosol with spray jets between 35 and 500 μl.

15. A process according to claim 14, wherein said first solvent is polyethylene glycol.

16. A process according to claim 14, wherein said first solvent is selected from the group consisting of glycerine-polyethylene glycoloxyoleate and glycerine-polyethylene glycol oxystearate.

* * * * *